United States Patent [19]
Kuehn et al.

[11] Patent Number: 5,470,341
[45] Date of Patent: Nov. 28, 1995

[54] HIGH VOLTAGE SWITCH DRIVE FOR IMPLANTABLE CARDIOVERTER/DEFIBRILLATOR

[75] Inventors: Kevin P. Kuehn, Birchwood; Martin A. Rossing, Ramsey; William C. Berg, Burnsville, all of Minn.

[73] Assignee: Medtronic, Inc., Minneapolis, Minn.

[21] Appl. No.: 165,448

[22] Filed: Dec. 10, 1993

[51] Int. Cl.⁶ ....................................................... A61N 1/39
[52] U.S. Cl. ..................................................... 607/5; 607/14
[58] Field of Search ................................................ 607/4.5

[56] References Cited

U.S. PATENT DOCUMENTS

| | | | |
|---|---|---|---|
| 4,800,833 | 1/1989 | Winstrom | 128/419 D |
| 4,830,006 | 5/1989 | Haluska | 128/419 PG |
| 4,850,357 | 7/1989 | Bach, Jr. | 128/419 D |
| 4,953,551 | 9/1990 | Mehra | 128/419 D |
| 4,998,531 | 3/1991 | Bocchi | 128/419 D |
| 5,163,427 | 11/1992 | Keimel | 128/419 D |
| 5,178,140 | 1/1993 | Ibraheim | 607/5 |

Primary Examiner—George Manuel
Assistant Examiner—Marianne Parker
Attorney, Agent, or Firm—Reed A. Duthler; Harold R. Patton

[57] ABSTRACT

A battery powered cardioverter or defibrillator employing a DC-DC converter for charging high voltage output capacitors and for delivering biphasic cardioversion or defibrillation pulses through a bridge circuit including high and low side drive circuits under the control of a microprocessor controlled arrhythmia detection system. Upon the detection of an arrhythmia and the selection of cardioversion/defibrillation therapy, the charging of the high voltage output capacitors is commenced and the capacitor voltage enables a regulated voltage source for the high and low side drive circuits for the high power IGTs of each branch of the bridge circuit. High voltage switching transients are suppressed from re-triggering or otherwise affecting operation of the drive circuits. Fail safe circuitry disables operation of the drive circuits in the event that the first and second control signals are inadvertently provided simultaneously or overlap.

11 Claims, 8 Drawing Sheets

HIGH VOLTAGE SWITCH DRIVE FOR IMPLANTABLE CARDIOVERTER/DEFIBRILLATOR

CROSS-REFERENCE TO RELATED APPLICATIONS

Reference is made to commonly assigned U.S. Pat. No. 5,265,588 and incorporated herein by reference.

BACKGROUND OF THE INVENTION

1. Field of the Invention

This invention relates to an implantable medical device that delivers sufficient electrical energy to cardiac tissue to defibrillate or cardiovert tachyarrhythmias and thus restore normal sinus rhythm and, more particularly, to improved driving circuits for controlling discharge of high voltage capacitors providing a biphasic cardioversion wave form shock.

2. Background Art

By way of definition, in the field of automatic implantable arrhythmia control devices, the term "cardioversion" or "cardioverter" refers to the process of and device for discharging relatively high energy electrical pulses into or across cardiac tissue to arrest a life threatening tachyarrhythmia. Cardioversion pulses may or may not be synchronized with a cardiac depolarization or rhythm and may be applied to arrest a malignant ventricular tachycardia or ventricular fibrillation with a selectable or programmable pulse energy. The arrest of ventricular fibrillation by such pulses is referred to as "defibrillation" (a form of cardioversion), and "defibrillators" have been characterized as a form of cardioverter. In the following description and claims, it is to be assumed that these terms are interchangeable, and that use of one term is inclusive of the other device or operation, unless specific distinctions are drawn between them in the context of the use.

Current implantable devices for the treatment of tachyarrhythmias, e.g. the MEDTRONIC Model 7217 PCD device, provide programmable staged therapies including anti-tachycardia pacing regimens and cardioversion energy and defibrillation energy shock regimens in order to terminate the arrhythmia with the most energy efficient and least traumatic therapies (if possible), as well as single chamber bradycardia pacing therapies. The Model 7217 PCD device provides a programmable energy, single polarity wave form, shock from the discharge of a high voltage output capacitor bank through a pair of electrodes disposed in relation to the heart.

Commonly assigned U.S. Pat. No. 5,163,427 to Keimel discloses an implantable cardioverter/defibrillator system which is capable of providing three defibrillation pulse methods, with a minimum of control and switching circuitry. The output stage is provided with two separate output capacitor banks which are sequentially discharged during sequential pulse defibrillation and simultaneously discharged during single or simultaneous pulse defibrillation through a two or three electrode system.

Other cardioversion pulse wave shapes have been proposed in conjunction with a variety of electrode systems in order to achieve more efficient cardioversion, including bi-phasic or multi-phasic wave form shocks generated in rapid sequence and applied to the same or separate electrode systems as described in the above referenced '107 application and in U.S. Pat. Nos. 4,800,833 to Winstrom, 4,830,006 to Haluska et al, 4,953,551 to Mehra, 5,178,140 to Ibrahim, and 4,850,357 to Bach. Despite the additional complexity, it is expected that cardioversion may be achieved more rapidly after the onset of an arrhythmia and at lower current consumption. In order to achieve low current consumption, these stimulation therapy regimens require rapid and efficient charging of high voltage output capacitors from low voltage battery power sources as well as efficient sequential (or simultaneous) discharge of the capacitors through the electrode systems employed.

Generally speaking, it is necessary to employ a DC-DC converter to convert electrical energy from a low voltage, low current power supply to a high voltage energy level stored in a high energy storage capacitor. A typical form of DC-DC converter is commonly referred to as a "flyback" converter which employs a transformer having a primary winding in series with the primary power supply and a secondary winding in series with the high energy discharge capacitors. An interrupting circuit or switch is placed in series with the primary coil and battery. Charging of the high energy capacitors is accomplished by inducing a voltage in the primary winding of the transformer creating a magnetic field in the secondary winding. When the current in the primary winding is interrupted, the collapsing field develops a current in the secondary winding which is applied to the high energy capacitors to charge them. The repeated interruption of the supply current charges the high energy capacitors to a desired level over time. Such DC-DC converters are disclosed in wherein charging circuits are disclosed which employ flyback oscillator voltage converters which step up the power source voltage and apply charging current to output capacitors until the voltage on the capacitors reaches the programmed shock energy level.

In sequential pulse, multi-phasic systems, two or more output capacitors are charged and discharged through separate discharge circuits arranged in a bridge circuit configuration so that the sequentially generated shocks applied to the same electrode pathway(s) have opposite polarity. The discharge of the high voltage capacitors is typically effected by connecting the charged capacitors to the electrodes in discharge circuit paths through high voltage, high current conducting, Insulated Gate Transistors (IGTs) or metal oxide semiconductor field effect transistors (MOSFETs or power FETs), either employed alone or in electrical series with high voltage thyristers or "triacs". In the above referenced '107 application and '006, and '427 patents, IGTs or power FETs are switched into conduction by dedicated drive circuits which respond to low voltage control signals.

These low impedance, high current conducting switches are necessary to make and break the series electrical connection of the high voltage capacitors with the electrode/ heart tissue load. The function of these switches must be tightly controlled to assure proper timing of the sequentially generated mono-phasic or bi-phasic shock impulses and to prevent destruction of the high voltage output circuit by the unintentional insertion of the switches directly across the high voltage capacitors. Noisy switch operation must also be suppressed.

In order to electrically isolate the high voltage discharge circuits from the low voltage control circuits and microprocessor based control system, isolation transformers or optical isolators (opto-couplers) or capacitive coupling and common mode rejection circuits have been proposed. In the '006, '357 and '531 patents, transformers are employed to couple discharge control signals to drive circuits. As stated in the '140 patent, such transformers are bulky, and the transformer cores are susceptible to external magnetic fields.

The optical isolators and driver circuits employed in the '427 patent do not suffer from these drawbacks, but the miniaturization of the opto-coupler components does result in large isolation capacitances. These capacitances can introduce switching transients when the discharge current is abruptly switched on and off, which could result in re-triggering through the driver circuit.

SUMMARY OF THE INVENTION

Accordingly, it is an object of the present invention to provide a highly energy efficient and compact circuit for driving high voltage switches in the output circuit of an implantable automatic cardioverter/defibrillator.

It is another object to provide a driving circuit for the high voltage switches of a cardioversion/defibrillation pulse generator that improves isolation between high and low voltage components and prevents transients from affecting the operation of the switches.

It is a further object to provide a cardioversion/defibrillation pulse generator that isolates the battery power supply for the low voltage control system from a separate low voltage power supply for the low voltage drive circuits of the high voltage switches in the high voltage output circuit without the addition of bulky components.

The above objects and attendant advantages are achieved in the context of a battery powered cardioverter or defibrillator employing a DC-DC converter for charging high voltage output capacitors and for delivering biphasic cardioversion or defibrillation pulses through a bridge circuit including high and low side drive circuits under the control of a microprocessor controlled arrhythmia detection system. Upon the detection of an arrhythmia and the selection of cardioversion/defibrillation therapy, the charging of the high voltage output capacitors is commenced and the capacitor voltage enables a regulated voltage source for the high and low side drive circuits for the high power IGTs of each branch of the high voltage bridge output circuit. Upon reaching full charge, the microprocessor provides first and second, bi-phasic pulse width defining, control signals in succession to separate inputs of each low side drive circuit which either provide a trigger signal to a high side drive circuit or a gate control signal to a low side IGT so that only one branch of the bridge circuit is enabled for conduction and discharge of the high voltage capacitors through the patient's heart during each phase. The respective high side drive circuit is triggered into producing a high side IGT gate control signal, and both IGTs of the branch are switched rapidly into conduction for the pulse width defined by the duration of the respective control signal.

In accordance with a particular aspect of the invention, high voltage switching transients are suppressed from re-triggering or otherwise affecting operation of the drive circuits. In this regard, discharge circuit means for delivering voltage stored on capacitor means to the heart in a discharge mode of operation and in response to a discharge control signal further comprises high voltage discharge control switch means operable in response to a switching signal for connecting and dis-connecting said high voltage capacitor means with the heart for discharging the capacitor means through the heart during the period of connection, voltage regulating means coupled to the capacitor means for sensing the voltage level stored on the capacitor means and for generating a regulated voltage upon charging of the capacitor means to a predetermined voltage level, drive circuit means powered by the regulated voltage and triggerable at an input terminal in response to said discharge control signal for providing the switching signal to the high voltage discharge control switch means, and means for inhibiting transient high voltage signals generated during switching of said high voltage switch means and coupled back to the input of the drive circuit means from re-triggering the drive circuit means.

In a further aspect of the invention, fail safe circuitry disables operation of the drive circuits in the event that the first and second control signals are inadvertently provided simultaneously or overlap.

The novel elements believed to be characteristic of the present invention are set forth in the appended claims. The invention itself, together with additional objects and attendant advantages, will best be understood by reference to the following detailed description, which, when taken in conjunction with the accompanying drawings, describes a presently preferred embodiment.

BRIEF DESCRIPTION OF THE DRAWINGS

Reference is now made to the accompanying detailed drawings of the preferred embodiments in which like reference numerals represent like or similar parts throughout, and wherein.

DETAILED DESCRIPTION OF THE PREFERRED EMBODIMENT

The present invention relates to the provision of biphasic cardioversion pulses or shocks in a cardioversion system that may or may not also have the capability of providing single or sequential monophasic cardioversion pulses or shocks. In the description of the preferred embodiment that follows, an implantable pacemaker/cardioverter/defibrillator in which the present invention is preferably implemented is capable of providing either single monophasic of biphasic cardioversion pulses or shocks which only require a pair of cardioversion electrodes. However, a variety of implantable lead and electrode systems may be employed, with more than one cardioversion electrode connected electrically in common to widen the cardioversion energy distribution across the heart. Such electrodes may include indwelling right ventricular, superior vena cava, and coronary sinus electrodes, active pulse generator case electrodes and/or epicardial and subcutaneous patch electrodes in various combinations of two or more. With a three electrode system, two of the electrodes are connected in common, and the energy distribution between the two common and the third electrode may lead to reduced energy sufficient to reliably cardiovert a heart in fibrillation or high rate malignant ventricular tachycardia.

Figure 1:
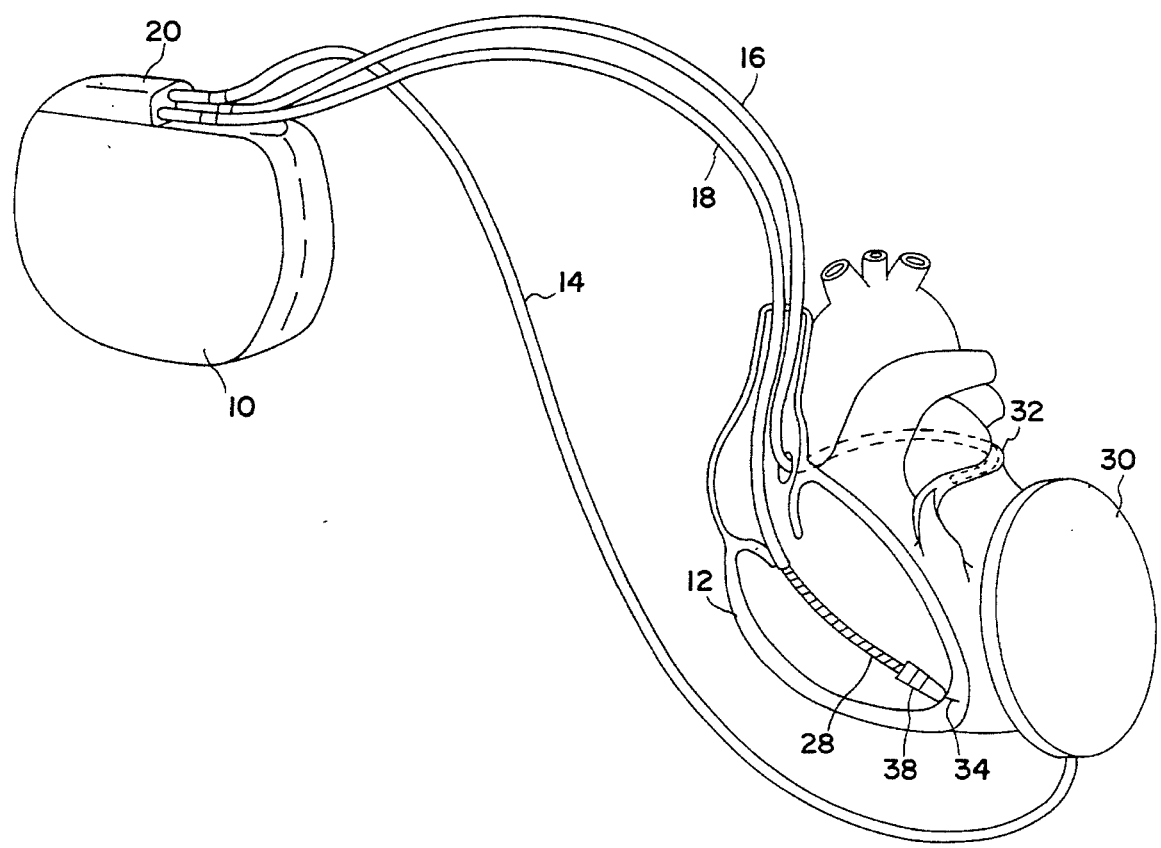
FIG. 1 is a drawing illustrating the physical components of a pacemaker/cardioverter/defibrillator and lead system of the type in which the present invention may be advantageously practiced.

FIG. 1 illustrates such an implantable pacemaker/cardioverter/defibrillator 10 and one possible selection of cardioversion electrodes on associated electrical leads 14, 16 and 18, and their relationship to a human heart 12. FIG. 1 corresponds generally to FIG. 1 of the '427 patent and '107 application except as noted below. The leads 14, 16, and 18 are coupled to the pacemaker/cardioverter/defibrillator 10 by means of a multi-port connector block 20, which contains separate connector ports for each of the three leads illustrated. Each of the leads 14, 16, 18 comprise a large surface area cardioversion electrode, and lead 18 also comprises a pair of pace/sense electrodes (making it a tripolar lead) all as described below. In implementation, it may be necessary to have a fourth port in connector block 20 and to use an adaptor to make the connections to the tripolar connector elements of lead 18. Moreover, if only two cardioversion electrodes are employed, then an insulating plug may have to be inserted into the unused port.

Unipolar lead 14 is coupled to a subcutaneous cardioversion electrode 30, which is intended to be mounted subcutaneously in the region of the left chest. Unipolar lead 16 is a coronary sinus (CS) lead employing an elongated coil, cardioversion electrode which is located in the coronary sinus of the heart. When positioned in the CS, the CS electrode extends around the heart from a point within the opening or ostium of the CS to a point in the vicinity of the left atrial appendage, as shown in broken line format at 32.

Tripolar lead 18 is provided with an elongated electrode coil 28 which is located in the right ventricle of the heart and functions as a third cardioversion electrode. Lead 18 also includes a first pace/sense electrode 34 and a second, closely spaced, pace/sense electrode 38. Electrode 34 takes the form of a distal helical coil which is screwed into the myocardial tissue of the right ventricle. The second pace/sense electrode 38 is closely spaced to the electrode 34 for bipolar pacing and near field electrogram or R-wave sensing in the apex of the right ventricle. A more detailed description of the leads illustrated can be found in the aforementioned '407 patent.

Through testing at implantation of cardioversion efficacy across one of the three electrodes with the other two electrodes in common or with each of the other electrodes alone, a selection may be made of the most efficacious electrode selection. If only two electrodes are needed, then the third lead and electrode may be eliminated. Typically, it is expected that all three of the electrodes will be employed, with two connected electrically in common internally within the pulse generator 10 as described below.

Figure 2:
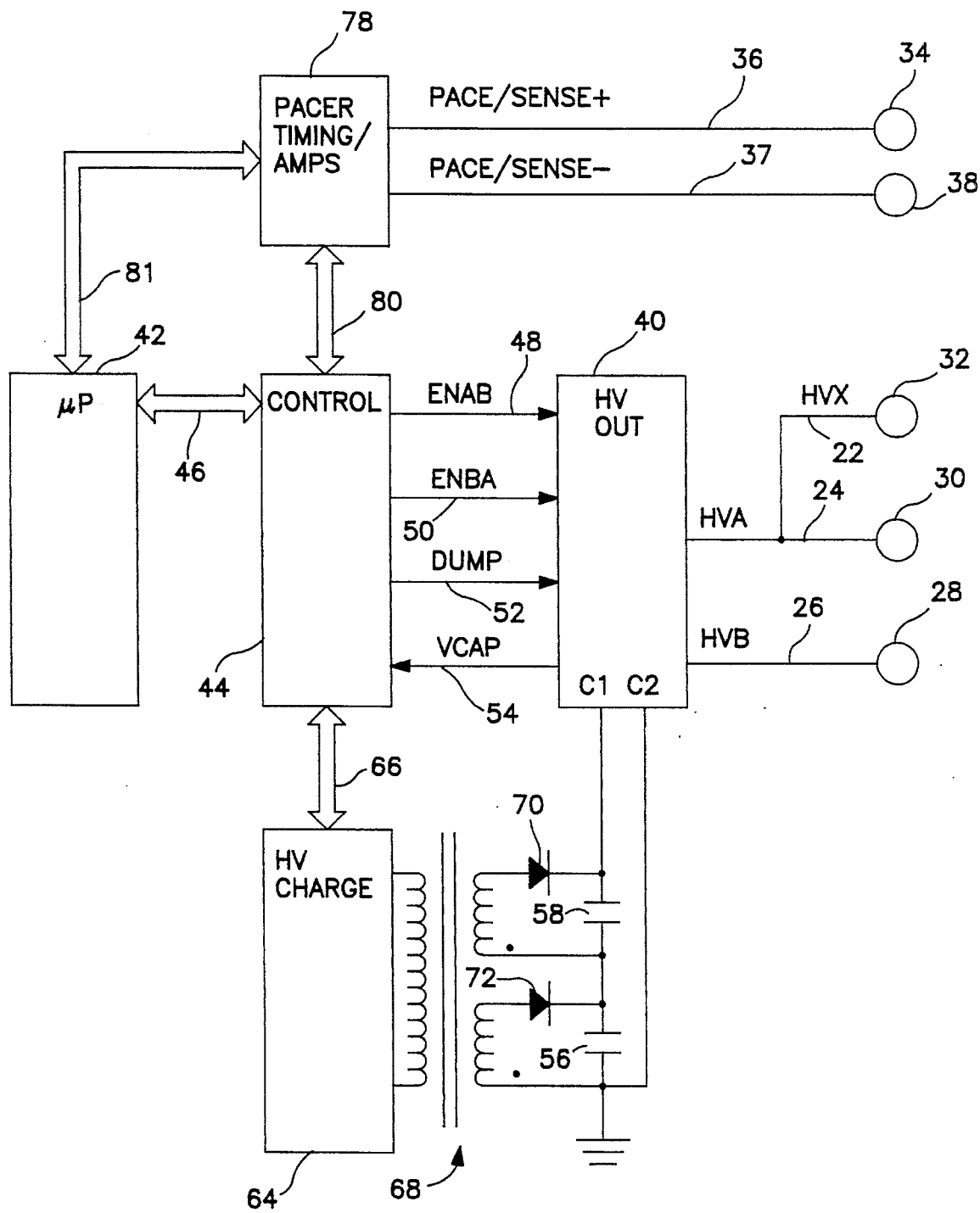
FIG. 2 is a functional block diagram illustrating the interconnection of the improved voltage conversion circuitry of the present invention with the primary functional components of an implantable pacemaker/cardioverter/defibrillator.

FIG. 2 is a block diagram illustrating the interconnection of a high voltage output circuit 40, a high voltage charging circuit 64 and capacitor bank 56, 58 according to one embodiment of the present invention with a prior art implantable pacemaker/cardioverter/defibrillator. As illustrated, the device is controlled by means of a stored program in a microprocessor 42, which performs all necessary computational functions within the device. Microprocessor 42 is linked to control circuitry 44 by means of a bi-directional data/control bus 46, and thereby controls operation of the output circuitry 40 and the high voltage charging circuitry 64. On reprogramming of the device or on the occurrence of signals indicative of delivery of cardiac pacing pulses or of the occurrence of cardiac contractions, pace/sense circuitry 78 will awaken microprocessor 42 to perform any necessary mathematical calculations, to perform tachycardia and fibrillation detection procedures and to update the time intervals controlled by the timers in pace/sense circuitry 78.

The control circuitry 44 provides three signals of primary importance to the output circuitry 40 of the present invention. These include the first and second control signals discussed above, labeled here as ENAB, line 48, and ENBA, line 50, which govern the timing and duration of the two phases of the biphasic cardioversion pulse or shock. Also of importance is the DUMP signal on line 52 which initiates discharge of the output capacitors, and the VCAP signal on line 54 which is indicative of the voltage stored on the output capacitors C1, C2, and is applied to the control circuitry 44.

Figure 3:
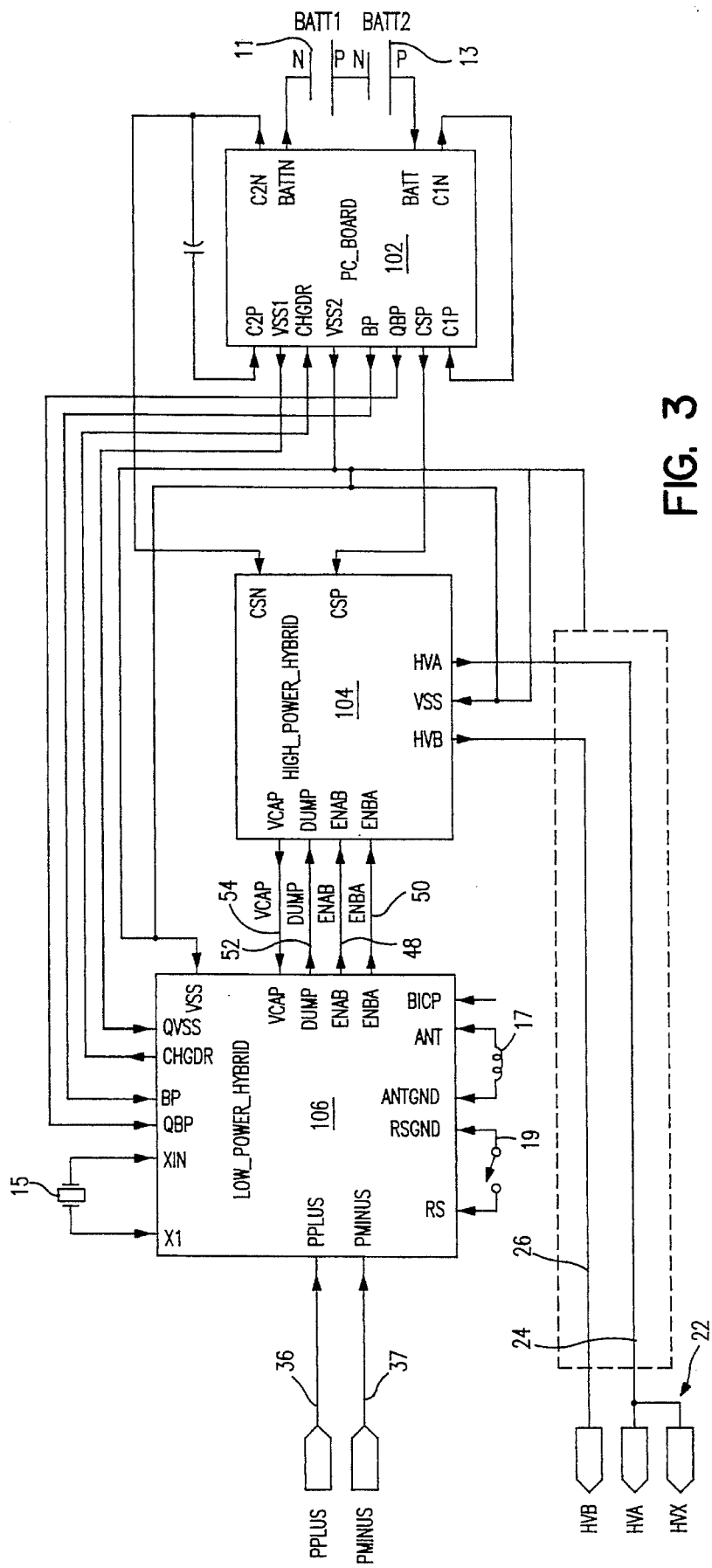
FIG. 3 is a schematic block diagram of the components of a preferred embodiment of the pacemaker/cardioverter/defibrillator employing a high voltage charging circuit.

As described above, a wide variety of cardioversion electrode bearing leads may be attached to two or all three cardioversion output terminals, labelled HVX, HVA, and HVB in FIG. 2, coupled to the connector block 20 bores. In the example illustrated in FIGS. 1 and 2, it will be assumed that the electrodes 28, 30 and 32 are coupled to the high voltage output circuitry 40 by means of connectors in the connector block 20 illustrated as conductors 22, 24 and 26, respectively. As shown in FIG. 3, conductors 22 and 24 labeled HVX and HVA are electrically connected in common so that only a monophasic or biphasic output shock may be delivered even if all three leads 18, 14 and 16 and electrodes 28, 30 and 32, respectively, are connected to the pulse generator as shown in FIG. 1 and described above.

The high voltage output circuit 40 includes a capacitor bank, including capacitors 56 and 58 and diodes 70 and 72, used for delivering defibrillation pulses to the electrodes. Alternatively, the capacitor bank may include a further set of capacitors as depicted in the above referenced '427 patent. In FIG. 2, the capacitor bank is illustrated in conjunction with the high voltage charging circuitry 64, controlled by the control/timing circuitry 44 by means of CHDR line 66. As illustrated, capacitors 56 (C1) and 58 (C2) are charged by means of a high frequency, high voltage transformer 68. Proper charging polarities are maintained by means of the diodes 70 and 72. VCAP line 54 provides a signal indicative of the voltage on the capacitor bank, and allows for control of the high voltage charging circuitry and for termination of the charging function when the stored voltage equals the programmed charging level.

The delivery of the biphasic cardioversion shock is controlled by the partial discharge of the voltage on the output capacitor bank in a first direction during a first phase logic signal on ENAB, line 48, and by further discharge of the remaining voltage in a second direction during closely timed second signal on ENBA, line 50. When ENAB is present, the first phase of the cardioversion pulse is delivered between the electrode(s) 30 and/or 32 and electrode 28. During a logic signal on ENBA, line 50, the second phase is delivered between in the opposite direction between the same electrodes.

Pace/sense circuitry 78 includes an R-wave amplifier according to the prior art, or more advantageously as disclosed in co-pending, commonly assigned application Ser. No. 07/612,670 by Keimel et al, for an "Apparatus for Monitoring Electrical Physiological Signals," filed Nov. 14, 1990, which is incorporated herein by reference in its entirety. However, the present invention is believed workable in the context of any known R-wave amplification system. Pace/sense circuitry 78 also includes a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80. Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 and ring electrode 38 of tripolar lead 18 through connector elements of the connector block 20 and associated adapters, if necessary, illustrated schematically as conductors 36 and 37.

The best mode of practicing the present invention known to the inventor is illustrated in conjunction with the design of a pacemaker/cardioverter/defibrillator employing the major circuit components depicted in FIG. 3 and the specific circuits of FIGS. 4 through 7. The present invention constitutes improvement in the voltage output circuitry for generating biphasic cardioversion shocks and may be practiced in connection with any cardioverter or defibrillator design. The particular circuitry involved in the implementation of the voltage output circuitry and further circuitry which supplies signals to operate the output circuitry are shown in specific detail. In the description of the preferred embodiment of FIGS. 3 through 7, a number of additional expressions for input and output signals or terminals than those described above are used throughout, including:

CHGDR—Charge drive signal for driving the on/off switch in the primary winding of the flyback transformer at a duty cycle established by the relative on and off times.

VSS—VSS is the circuit ground which may also appear labeled QVSS and may be connected to BATTN.

BATT—Battery positive power supply which may also appear as B+ or as BP.

BATTN—Battery negative power supply.

PPLUS—Plus terminal for the pace/sense function.

PMINUS—Negative terminal for the pace/sense function.

ENBA—Enable signal commanding capacitor discharge from HVB to HVA (and HVX) and setting the duration of one phase of the biphasic pulse.

ENAB—Enable signal commanding capacitor discharge from HVA (and HVX) to HVB and setting the duration of the other phase of the biphasic pulse.

CSP—Charge store positive terminal.

C1P—Capacitor 1 positive terminal connection.

C1N—Capacitor 1 negative terminal connection.

C2P—Capacitor 2 positive terminal connection.

C2N—Capacitor 2 negative terminal connection.

CSN—Charge store negative terminal.

VDD—Internally generated programmable regulated power supply.

DUMP—DUMP signal initiates the internal self discharge of the capacitors C1, C2 to a load impedance.

OPTIN—Input terminal to the drive circuit optionally connected to an opto-coupler.

VIN—Input terminal to the drive circuit optionally connected to an input signal source.

VOUT—Output terminal of the drive circuit for supplying VDD voltage.

CSEN—Enable signal input terminal of the drive circuit optionally coupled to receive an opto-coupler command signal.

CSOUT—Output terminal of the drive circuit optionally coupled to drive an opto-coupler.

Other acronyms may appear in the description of the following drawings which will be explained as necessary to understand the manner in which the present invention may be practiced in its preferred embodiment.

Turning now to FIG. 3, the major circuit components of the pacemaker/cardioverter/defibrillator of the present invention are depicted and they include the batteries 11 and 13, the PC board 102, the high voltage output capacitors C1, C2 (56, 58 in FIG. 2), the high power hybrid board 104, the low power hybrid board 106, the crystal 15, the antenna 17, and the reed switch 19. The batteries 11 and 13 are coupled to the BATT and BATTN inputs of the PC board 102. The crystal 15 is coupled to the X1 and X1N inputs of the low power hybrid 106. The antenna 17 is coupled between the ANT and ANTGND inputs of low power hybrid 106 and the reed switch 19 is coupled between the RDSW and RSGND inputs of low power hybrid 106. The PPLUS and PMINUS terminals are coupled to respectively labeled pins of the low power hybrid 106, which contains the pace/sense circuitry 78 of FIG. 2.

The low power hybrid 106 includes the basic timing and control circuitry of the system, including the programming and telemetry functions, the electrogram sensing and pacing functions, the microprocessor and RAM/ROM memories, all implemented in both digital and analog circuits corresponding to blocks 42, 44 and 78 in FIG. 2. The low power hybrid 106 develops the CHGDR signal as well as the DUMP, ENBA and ENAB signals relevant to the operation of the high voltage output circuit of the present invention.

The PC board 102 corresponds to the high voltage charging block 64 in FIG. 2, and also includes the step up transformer 110 and diodes 121, 123. The relatively large output capacitors C1, C2 are electrically connected to the PC board 102 through the input terminals C1N and C1P and C2N and C2P, respectively. The PC board 102 presents the charge storage positive and negative signals CSP and CSN, respectively, to the high power hybrid 104. PC board 102 also includes an on-off control switch, responsive to the CHGDR signal from the low power hybrid 106, for supplying stepped up, rectified current to the output capacitors C1, C2, across which the voltage signals CSP, CSN are developed.

The high power hybrid 104 corresponds to the high voltage output block 40 illustrated in FIG. 2 and includes switching circuitry for delivery of voltage stored in capacitors C1 and C2 as monophasic and biphasic output pulses. Delivery of the output pulses is controlled by the low power hybrid 106 via ENAB and ENBA lines 48 and 50, respectively. Similarly, the HVA line 24, which is coupled in common to the HVX line 22, and the HVB line 26 are coupled to the HVA and HVB output pins of high power hybrid 104. The high voltage discharges forming the biphasic or monophasic cardioversion shocks are generated from the high power hybrid 104 and conducted to the HVA and HVB output terminals and the cardioversion electrode system employed as described above.

Figure 4A:
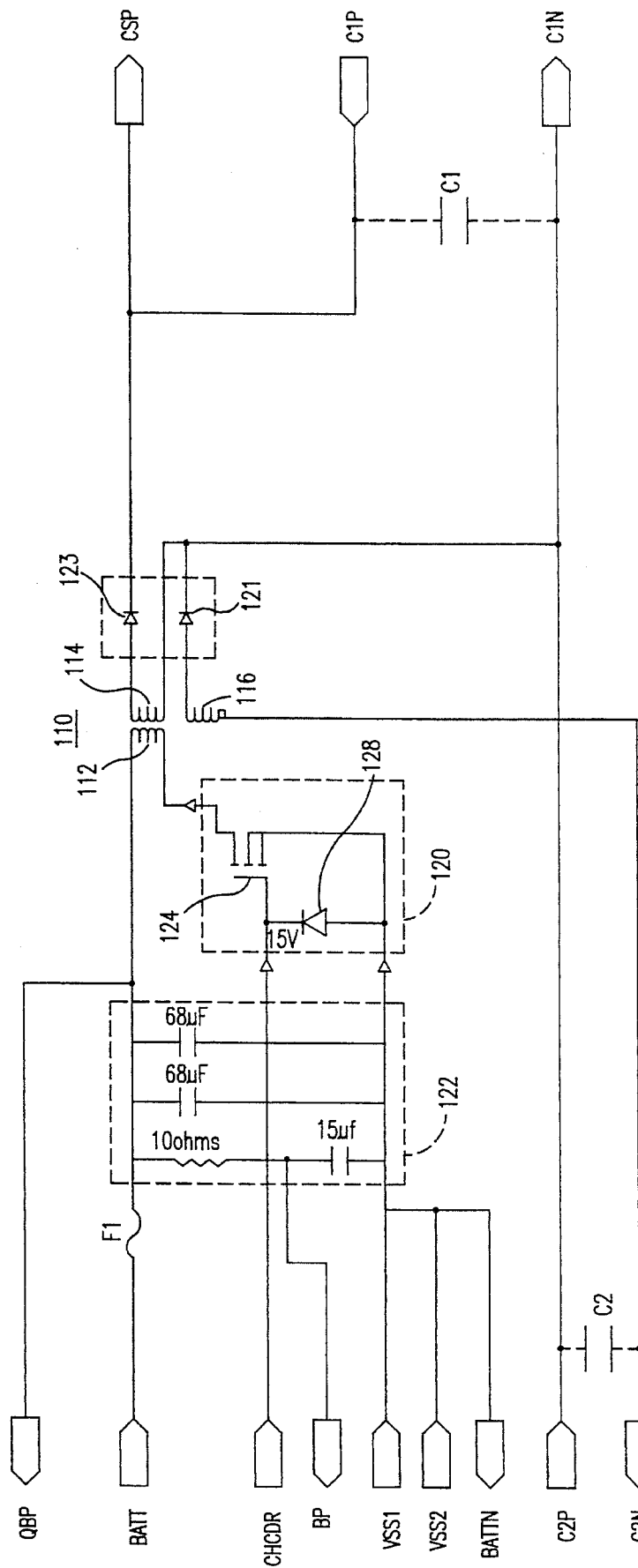
FIGS. 4A and 4B are an electrical schematic diagram of the high voltage charging circuit, output capacitor bank and high voltage output circuit of the present invention.

FIG. 4A illustrates the PC board 102 in more detail. The step-up transformer 110 includes a primary winding 112 and secondary windings 114, 116, which are coupled through diodes 121 and 123 to the output capacitors C1, C2. As described above, the voltage across output capacitors C1 and C2 is applied at output terminals C1P, C1N and C2P, C2N to correspondingly labeled terminals in FIG. 4B.

The primary winding 112 is coupled at one terminal to the power supply BATT input terminal through a fuse link F1 and at its other terminal to the BATTN/VSS terminals through the duty cycle switching circuit block 120. A filter network of resistors and capacitors 122 are coupled across the BATT and BATTN/VSS terminals.

The switching circuit 120 includes an IGT or power FET or 124 having its source and drain terminals coupled across a zener diode 126 in such a fashion that when the power FET 124 is rendered conductive by a CHGDR signal applied at its gate input terminal, it allows current to pass through the primary coil 112 of the step-up transformer 110. Power FET 124 preferably has a very low drain-to-source impedance when conductive and a high gate impedance. A second zener diode 128 coupled to the gate terminal of the power FET 124 and having a reverse breakdown voltage of around 15 volts provides ESD protection for the power FET 124.

The CHGDR signal amplitude is generated as a function of the BATT voltage and a frequency which is established by a VCO as a function of the VCAP voltage. The "on" time of the CHGDR signal is constant and is preferably 11 microseconds (except when the BATT potential is depleted as explained hereafter), whereas the off-time is variable in inverse proportion to the VCAP value.

The frequency at which the primary is driven ("on" time) and then open circuited ("off" time) is controlled by a VCO whose period equals a constant "on" time plus a variable "off" time which is inversely proportional to the DC value Vm of the voltage stored on the output capacitors. The expression for the period of the VCO is:

$$\text{Period} = \text{Ton} + \frac{K}{IF + Vm/R},$$

Further description of how the CHGDR signal is generated may be obtained in the above referenced '107 application and forms no part of the present invention.

Figure 4B:
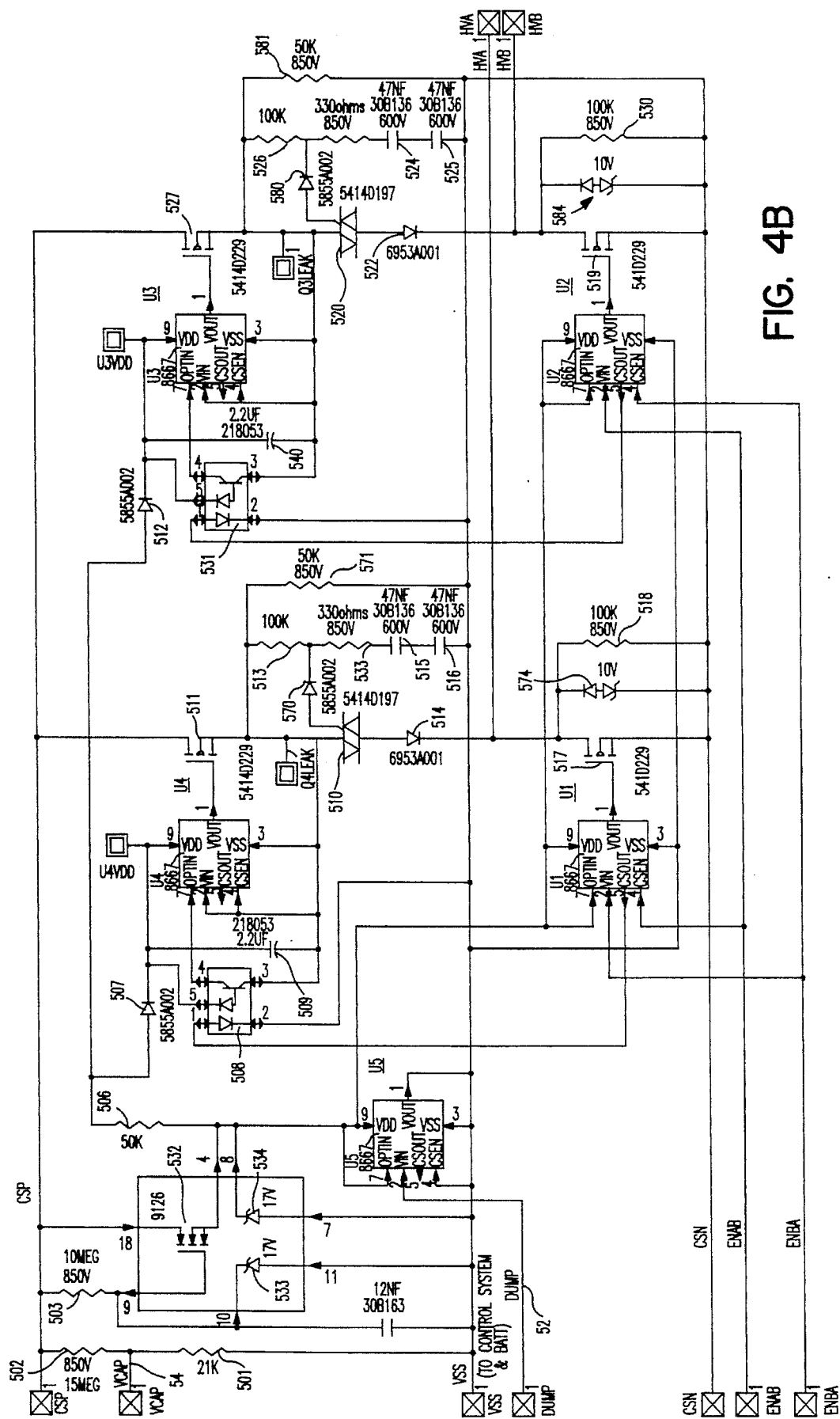

Reference is now turned to the high power hybrid schematic diagram depicted in FIG. 4B. This high power hybrid electrical schematic diagram is similar to but not identical to FIG. 3 of the above incorporated '427 patent and the '551 patent and is similar to FIG. 4B of the above-referenced '107 application. FIG. 4B is set forth in its entirety to present an alternative embodiment to the embodiment of FIG. 3 of the '427 patent and the '551 patent in which the present invention may be practiced. However, it will be understood that the invention may be practiced in the context of any of the referenced voltage converters.

In particular, in FIG. 4B, the VCAP signal on line 54 is derived from and representative of the actual voltage on the output capacitors C1, C2 across terminals CSP, CSN/VSS in FIG. 4B. The VCAP signal is developed across the CSP and CSN/VSS terminals through a voltage divider comprising resistor 501 (21K ohm nominal) and resistor 502 (15 Megohm). Thus, the VCAP signal is proportional to the "positive, summed voltages" of the capacitors C1 and C2 from FIG. 4A with respect to ground potential.

The VCAP signal is employed in the low power hybrid 106 of FIG. 3 to monitor the state of charge of the output capacitors C1 and C2 for various operations, including the determination of when the voltage on the output capacitors C1, C2 has reached the desired level to initiate the delivery of the cardioversion/defibrillation shocks through discharge of the capacitors C1, C2 for a predetermined interval. The interval may be a selected interval or may be a function of the magnitude of the VCAP signal as the capacitors are discharged. In other words, the discharge may be for a predetermined time interval or until the voltages have discharged to a desired level. By controlling the discharge level, the amount of energy delivered to the heart is directly controlled.

In FIG. 4B, the voltage at terminal CSP is connected to two parallel discharge circuits (referred to with the load presented by the patient's heart as a "bridge" or "H" circuit) and back to the terminal CSN in order to provide first and second direction discharge paths through the heart coupled between the terminals HVA and HVB. The terminals 24 (HVA) and 26 (HVB) are connected to the junction of the diodes 514 and 522 with the drains of the IGT's or power FETs 517 and 519, respectively. Resistors 518, 530 and back-to-back diodes 574, 584 are coupled across the sources and drains of power FETs 517 and 519.

The selection of the first and second discharge paths is made by the ENAB and ENBA signals both applied to the low side drive circuits U1 and U2. The AB discharge path is from the terminal 24 (HVA) through the heart and to the terminal 26 (HVB), and the discharge path BA is from the terminal 26 (HVB) through the heart and to the terminal 24 (HVA). The entire discharge path AB includes the terminal CSP, the high side IGT or power FET 511, triac 510, diode 514, terminal HVA, the patient's heart, terminal HVB, low side IGT or power FET 519, and terminal CSN. Similarly, the discharge path BA is from the terminal CSP through high side IGT or power FET 527, triac 520, diode 522, terminal HVB, the patient's heart, terminal HVA, low side IGT or power FET 517 and terminal CSN.

Before explaining the switching of the high and low side IGTs and triacs, it should be noted that the power supply for operating the drive circuits of FIG. 4B is obtained from the potential across terminals CSP and CSN by a power supply comprising the power FET 532 and zener diodes 533, 534 within IC block U8. The components in block U8 are coupled to the VDD power line in order to provide a regulated voltage to the VDD terminals of the drive circuits U1–U4 (and to certain associated circuit components), which control the switching of IGT's 511, 517, 519, 527, and drive circuit block U5, which controls internal discharge of C1, C2 (FIG. 4A) in response to a DUMP command.

The FET 532 in U8 has its source and gate normally biased at 17 volts by the zener diodes 533 and 534, respectively. The drain voltage may be from zero volts to 1,000 volts, depending on the state of charge of the capacitors C1, C2 (FIG. 4A). When the drain voltage exceeds the gate bias of 17 volts, the FET 532 is rendered conductive with about a 2–3 volt drop across its gate and source terminals, causing the source terminal to present a nominal 14.5–15 volt regulated voltage at the terminal 4 of block U8. The zener diode 534 remains reverse biased at this voltage, so the source terminal voltage is stabilized.

The terminal 4 of the block U8 is coupled to the VDD and OPTIN inputs of the drive circuit U5 and to resistor 506. A DUMP command is presented during testing of the charging circuit after charging has been initiated and there is no intention to discharge the voltage through the patient's heart. When the DUMP command is present, the 15 volt regulated voltage is applied through the VDD terminal of drive circuit U5 through a 1 volt drop to the VOUT terminal. The VOUT terminal is coupled directly to VSS, but it presents an output impedance of about 1K ohm to the applied voltage. The output impedance thus develops a 14 mA current to the source of the FET 532 in block U8, causing the voltage on C1, C2 to drain through the FET 532 and the output impedance over a relatively long period of time, nominally 12 seconds. The DUMP command is applied for a period of 20 seconds to assure full discharge. In the event that the capacitors C1, C2 are charged but not discharged automatically into the patient's heart or discharged via a DUMP command, then the voltage on capacitors C1, C2 would self-discharge through the high impedance resistors 501, 502 over a period of minutes to hours.

Returning to the bridge circuit, the power FET's 511 and 527 are the high voltage side switching IGT's whose on and off operation are controlled by opto-isolators 508 and 531 and drive circuits U3 and U4. The low voltage side power FET's 517 and 519 are switched on or off by the drive circuits U1 and U2 which, in addition, develop the switching signals for the opto-couplers 508 and 531, respectively. The triacs 510 and 520 are switched on by the power surge through the respective power FET's 511 and 527 and by the current drawn through the diodes 570, 580 to the respective trigger junctions to charge the RC timing circuit components (capacitors 515, 516, 524, 525 and resistors 529, 533, 571, 581) coupled to each of the trigger input terminals and VSS.

The ENAB signal is applied to terminal CSEN of drive circuit U1 and terminal VIN of drive circuit U2. The ENAB signal applied to terminal CSEN of drive circuit UI provides a current drive signal out terminal CSOUT to the LED of opto-coupler 508. The LED emits light which is detected by the associated photo diode, and it is rendered conductive, which in turn renders the associated transistor (both shown in opto-coupler block 508) conductive. When this occurs, current is drawn from the OPTIN terminal of drive circuit U4, and a nominal 14.5 volt signal developed from VDD through a FET voltage drop is applied at the VOUT terminal to the gate of the IGT 511 to drive it into conduction and hold it in conduction for the duration of the ENAB signal. The current drawn from the OPTIN terminal exceeds a threshold and is recognized as an asserted state by the drive circuit U4 in a manner to be described with reference to FIG. 5.

The ENAB signal is also applied to the VIN input terminal of drive circuit U2, which in turn provides the 14.5 volt regulated supply signal from its VOUT terminal to the gate of IGT 519. In this fashion, IGTs 511 and 519 are rendered conductive, triggering conduction of triac 510, and the AB discharge circuit path is closed to allow discharge of the shock through the heart in the "AB" discharge path direction.

In like fashion, the ENBA signal is coupled to the charge drive circuits U1, U2 and the opto-coupler 531 to complete the "BA" discharge path by switching on IGTs 517 and 527.

Figure 5:
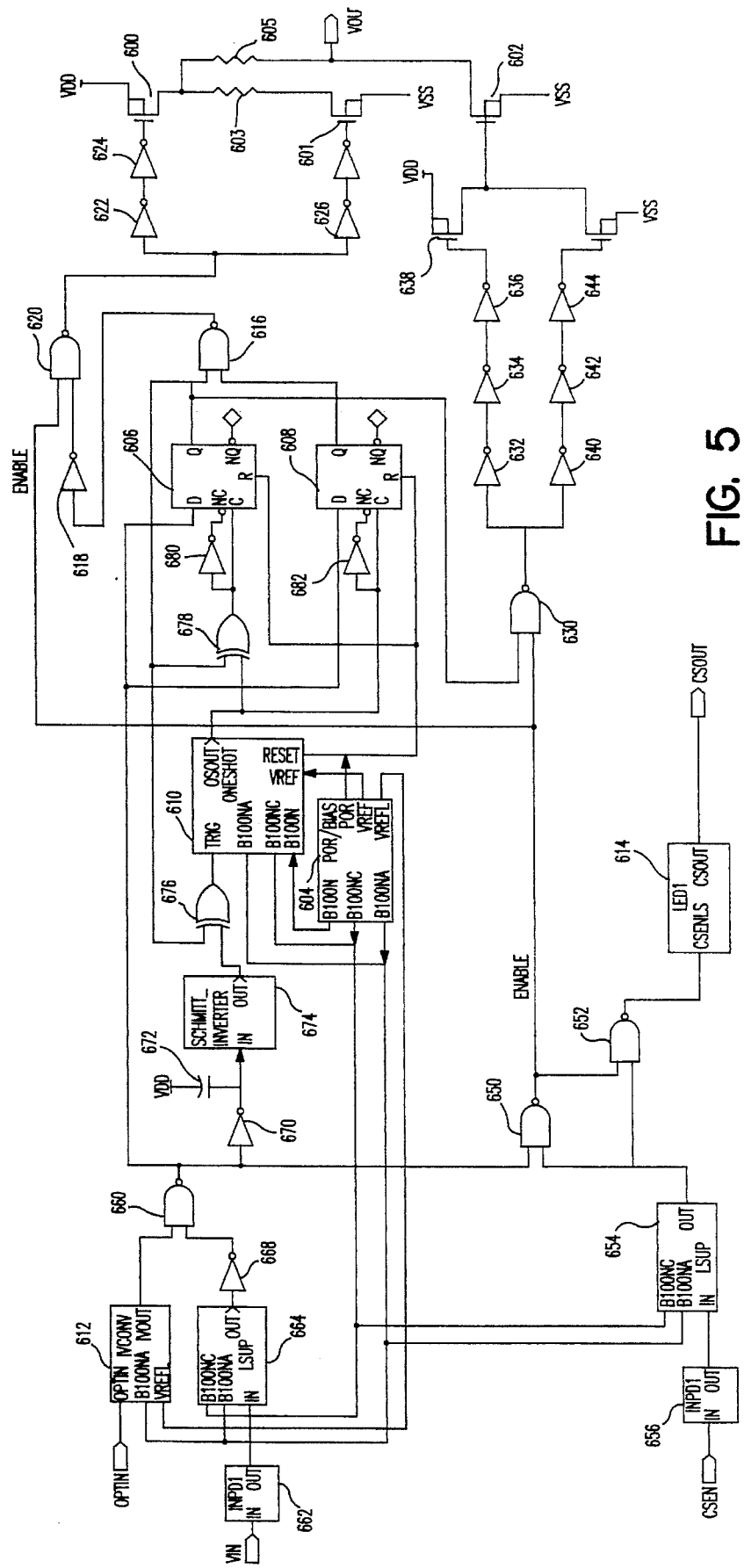
FIG. 5 is an electrical schematic diagram of a drive circuit of the present invention employed in FIG. 4B.

Turning now to FIG. 5, it depicts an improved circuit block diagram that is employed in each of the drive circuits U1–U5. The drive circuit of FIG. 5 functions differently when connected as high side drive circuits U3 and U4 than as low side drive circuits U1 and U2 and as the regulated voltage source U5 as described generally above. The input signals differ, but in each case a 14.5 volt output signal at output terminal VOUT is provided by coupling the regulated power supply VDD provided at pin 4 of block U8 to that terminal through a conducting FET in response to a positive signal at the VIN terminal or an asserted current signal drawn from the OPTIN terminal. The drive circuit of FIG. 5 configured as a low side drive circuit U1 and U2 has its OPTIN terminal coupled to its VDD terminal, so that only an ENBA or ENAB signal applied at the VIN input terminal will switch VDD to the VOUT terminal. A positive ENBA or ENAB signal at its CSEN input terminal produces a positive drive signal at its CSOUT terminal to drive the LED of the associated high side drive circuit into conduction to emit light as described above.

The drive circuit of FIG. 5 operating as a high side drive circuit in the bridge circuit is explained as follows in reference to the input and output connections depicted in FIG. 4B. In accordance with the present invention, the drive circuits U3 and U4 are designed to prevent the high voltage side IGTs 527 and 511, respectively, from being inadvertently switched off and on in an oscillatory pattern due to switching transients which can occur in the components of the opto-couplers 508 and 531 upon the conduction and extinction of the associated IGTs. In this regard, the IGTs 511 and 527 are rendered conductive and non-conductive at a slew rate of 1 Volt/nsec., and high voltages of up to 800 VDC are rapidly applied to or removed from the emitters of the transistors of the opto-couplers 508 and 531. The miniaturized components of the opto-couplers have small parasitic capacitances of about <0.5 pF between the emitter and base of the transistor and across the isolation boundary between the LED and the photo diode. This parasitic capacitance conducts momentarily due to the high slew rate and removes charge from the base of the transistor, causing it to cease conducting and drawing current from the OPTIN terminal.

Once the voltage slew rate diminishes, the transistors of the opto-couplers 508 and 531 remain conductive for the duration of the ENAB and ENBA signals, respectively, acting through the low side drive circuits. At the start of an ENAB signal causing an LED drive signal at the CSOUT terminal of drive circuit U1, for example, the transistor of the opto-coupler 508 is instantly rendered conductive. But, during the high slew rate transition at the drain of IGT 511, the transistor may be momentarily turned off until it stops conducting in the reverse direction, causing the drive circuit U1 to stop providing the 14.5 volt signal at the gate of IGT 511, turning it off. This momentary or transient turn-off of both of the drive circuits U3 and U4 must be ignored, or the system may go into damped oscillations. In the same fashion, at the termination of the ENBA and ENAB signals, the slew rate of the transition and the parasitic capacitances may also initiate damped oscillations.

In addition, it is also necessary to prevent the inadvertent simultaneous delivery of the positive ENBA and ENAB command signals from causing the four IGTs 511, 517, 527 and 530 to conduct simultaneously. The circuit of FIG. 5 is designed to prevent the VDD voltage from being presented at the CSOUT and VOUT output terminals when positive signals are applied at both the CSEN and VIN input terminals.

When the output capacitors C1, C2 are charging or charged, the regulated voltage at VDD is established as described above, and the drive circuits U1–U4 are in an active quiescent state. The voltage VDD is shown in FIG. 5 in the output circuit coupled to the drain of FET 600 and coupled to the capacitor 672. Although not shown in FIG. 5 in each case, it will be understood that VDD, as well as system ground VSS, are applied to power the components of each of the depicted circuit blocks, gates and inverters.

After the regulated supply voltage VDD is established, the signal output level at each terminal VOUT is held low by the conduction of FETs 601 and 602 in a manner to be described. Until the signals ENBA or ENAB are generated by the system controller low power hybrid 106 and the drive circuit operates, FET 600 is non-conductive. Similarly, the LED driver circuit 614 does not provide an output signal at the CSOUT terminal, in the case of the low side drive circuits.

In order to assure that the drive circuit operates properly on a transition to the active state, a power-on-reset and bias or POR/BIAS circuit block 604 is provided that generates a set of reference biasing and reset signals each time that the regulated voltage VDD is brought up by the charging of the output capacitors C1, C2. The signal POR is developed to reset the flip-flops 606 and 608 to insure that the Q outputs of both are low and to reset the timing of the one shot circuit block 610. First and second reference voltage signals VREF and VREFL are also generated by POR/BIAS block 604 and applied to the one shot circuit block 610 and the current to voltage converter and comparator or IVCONV block 612, respectively. The signal VREF is applied to the one shot 610 as the reference voltage to which the voltage that an internal timing capacitor is charged to when the one shot is triggered at its TRIG terminal; its level is selected to be higher than VREFL to enable the use of a smaller timing capacitor. The reference signal VREFL is a lower voltage for better noise immunity and is employed in a comparator in IVCONV 612 for comparison to a voltage level converted from the current level drawn from the OPTIN terminal.

The POR/BIAS block 604 also provides a set of p-channel referenced bias voltages B100N and B100NC for biasing cascoded current sources and B100NA for biasing current sources that are not cascoded in the level shifter or LSUP blocks 654 and 664, the one shot 610 and the IVCONV 612 described as follows.

Once a transition has been made from an unpowered quiescent state to the powered or active quiescent state, each of the circuit blocks is powered and biased, and the Q outputs of the flip-flops 606 and 608 are reset to low. The low state of the Q outputs causes the NAND gate 616 output state to be high, and that state is inverted by inverter 618 and applied as a low logic state signal to one input of the NAND gate 620. The other input of NAND gate 620 is coupled to the ENABLE output of NAND gate 650, which is at a low logic state, and the output thereof is at a high logic state. The high logic state voltage is twice inverted by two parallel sets of inverters 622, 624 and 626, 628, to provide higher gain. The inverted high logic state signals are applied to the gates of the output stage FETs 600 and 601, respectively. FET 600 is biased off, and FET 601 is forward biased and conductive through the current limiting resistors 603 and 605 to provide a controlled rate of turn-off of the associated IGT through the RC circuit of the resistors 603, 605 and the drain-to-gate parasitic capacitance of the IGT.

In the active quiescent state, the FET 602 is also biased into conduction in order to short circuit the parasitic capacitance and drain current from the gate of the IGT coupled to the VOUT terminal. FET 602 is biased on by voltage VDD applied to its gate through the conduction of FET 638. FET 638 is rendered conductive and FET 646 is rendered non-conductive due to the high logic state at the output of NAND gate 630. In this state, the Q output of flip-flop 606 is at a logic low state by action of the POR/BIAS block 604, and it is connected to one input of the NAND gate 630. In the active quiescent state, the other input of NAND gate 630 is normally high, and so the output of the NAND gate 630 is set high when the flip-flop 606 is reset and stays high until the flip-flops 606 and 608 change state. The high output state is thrice inverted in two parallel paths by inverters 632, 634, 636 and 640, 642, 644, and the resulting low logic state signals are applied thereby to the series connected FETs 638 and 646, respectively. FETs 638 and 646 are biased on and off, respectively, and the current applied to the gate of FET 602 tends to draw it into conduction when it is forward biased through the VOUT terminal. A pair of current limiting resistors 603 and 605 couple the FETs 600 and 601 to the terminal VOUT. In this state the voltage VDD is not coupled to VOUT, and current flow through the FETs 638, 601 and 602 is limited.

Also, during the active quiescent state, the CSOUT terminal of LED current source providing block 614 is held low. In order to provide drive current and voltage to the input LED in the opto-couplers, a current source is required as described above. The specification for the current sourced from output terminal CSOUT is 7 mA<I<30 mA. The CTR (current transfer ratio) of the external opto-coupler is specified as a minimum of 15% at 16 mA. Consequently the resulting output current from the opto-coupler will have a minimum of approximately 1.0 mA. This is necessary to guarantee turn-on of the high side drivers U3 and U4 in a manner which is as immune to parasitic effects as possible.

The LED driver block 614 is preceded by the dual input assertion lockout NAND gates 650 and 652, an input level shifter LSUP 654 and an input protection circuit INPD block 656. The input signal to the terminal CSENLS of the LED driver block 614 must be low in order to develop the requisite drive current and voltage. The input signal is inverted internally in LED driver block 614.

Turning to the operation of the LED driver portion of the drive circuit of FIG. 5, it is only employed in the low side drive circuits U1 and U2. As described above, the ENBA and ENAB signals are generated by the controller IC and delivered to first one and then the other CSEN input terminal of the drive blocks U1 and U2, respectively. These positive going or high logic state signals are passed through the INPD block 656 and applied to the input terminal of the LSUP block 654. The LSUP circuit block 654 provides a non-inverting input level shift function from the input logic levels of 0 to 2.1 VDC to the output drive levels of 0 VDC to 9–18 VDC.

The high output signal of LSUP block 654 is applied to an input terminal of the NAND gates 650 and 652 which are connected to the other input terminal of the NAND gates 620 and 630. The NAND gates 650 and 652 provide protection of the high voltage output circuit in the event that an ENAB and an ENBA signal are applied simultaneously to the VIN and CSEN terminals of the low side drive circuits U1 and U2. In such a case, the high output signals of the LSUP block 654 and the NAND gate 660 would drive the output of NAND gate 650 low, and its low output state would drive FET 602 into conduction (through components 630–646), forcing the VOUT terminal to VSS. The low output of the NAND gate 650 (i.e., the absence of the ENABLE signal) renders the NAND gate 630 incapable of switching to a low state at its output regardless of the signal level at its other input. Similarly, the low output of NAND gate 650 disables NAND gate 620, and it is incapable of switching to or maintaining a high output, which renders FET 600 non-conductive.

The low output state of NAND gate 650 also inhibits the operation of the LED driver circuit 614 by forcing the output of NAND gate 652 high. The high output signal at the LED driver circuit 614 input terminal CSENLS turns the LED driver circuit 614 off. Thus, the high side drive circuits U3, U4 are maintained off in the event that the ENAB and ENBA signals are asserted simultaneously.

Assuming the absence of simultaneously asserted ENBA and ENAB signals or any other situation where the output states of NAND gate 660 and LSUP block 654 are both high, the output of NAND gate 650 stays high and the output of NAND gate 652 goes low in the presence of a level shifted output signal from LSUP 654 in response to an ENBA or ENAB signal at the CSEN input terminal. The LED driver block 614 supplies the current and voltage specified above to the LED of the associated opto-coupler for the duration of the ENBA or ENAB signal as described above.

Figure 6:
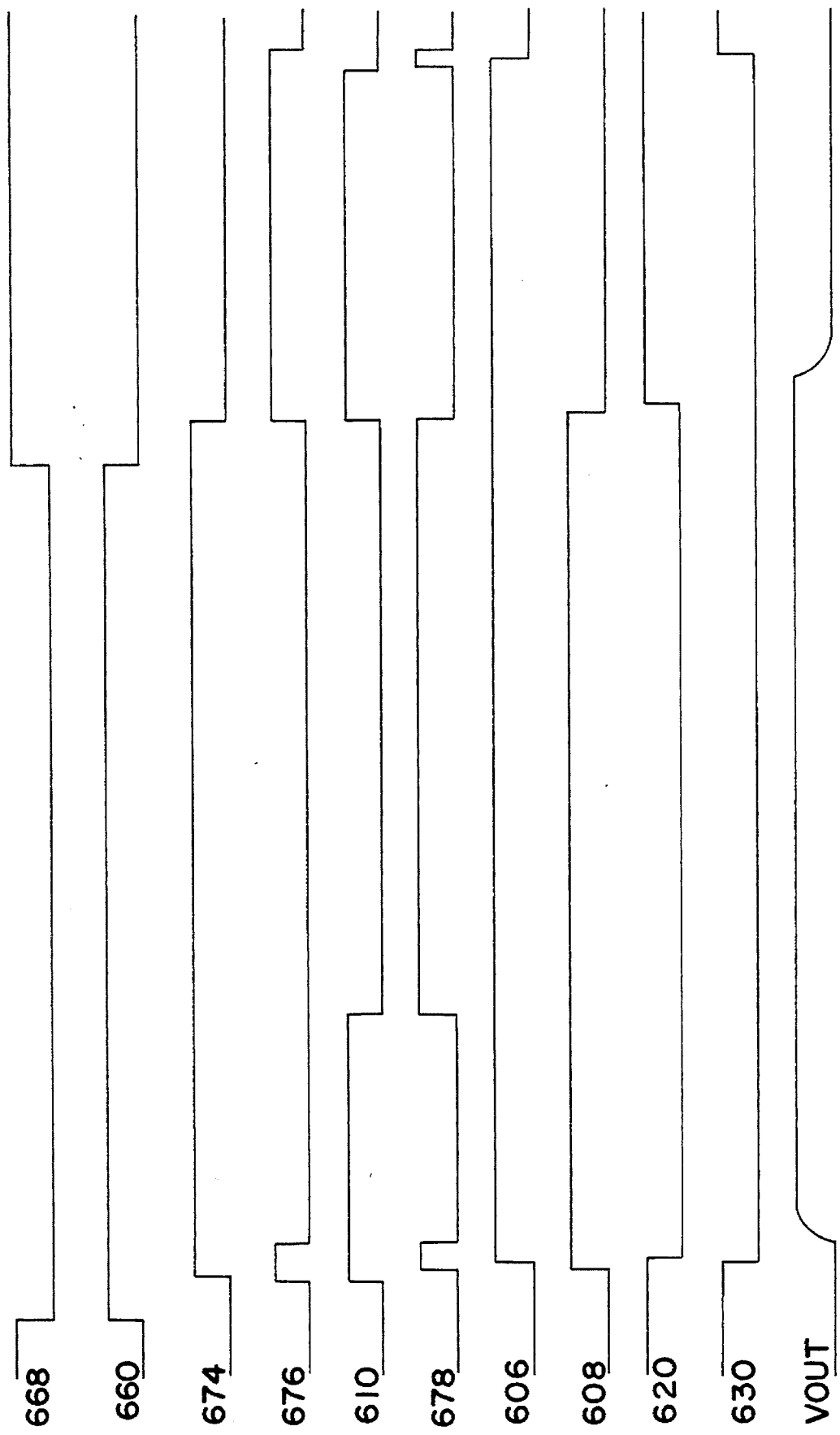
FIG. 6 is a timing diagram depicting an operation of the circuit of FIG. 5 configured as a low side drive circuit in FIG. 4B.

Turning now to the detailed operation of the switching circuitry for rendering FET 600 conductive and assuring the non-conduction of FETs 601 and 602, first the circuit of FIG. 5 and its operation as shown in FIG. 6 will be described in relation to the drive circuits U1 and U2 and the DUMP circuit U5. In these configurations, this operation is completed by the assertion of the ENBA or ENAB or DUMP signals at the VIN input terminals. The OPTIN terminals in each case are coupled to VDD, and the output of the current to voltage converter and comparator or IVCONV 612 is always high. The VDD level is compared to the VREFL value in IVCONV 612, resulting in the high output always present at one input of NAND gate 660.

In regard to FIG. 6, the output signals or states of the numbered components of FIG. 5 are depicted in response to the VIN signal level as inverted by inverter 668. The pulse widths depicted are exaggerated for illustration of the functions and relative timing and are not to scale. The positive logic signal at the VIN terminal is passed through an INPD block 662, and the positive going output signal is applied to the INPUT terminal of a further LSUP 664 which again level shifts the signal to a higher voltage as described above. The level shifted signal is inverted by inverter 668 and applied to the other input terminal of NAND gate 660. In the absence of a detected signal at VIN, the inverter 668 assures that the output of the NAND gate 660 is low, since both inputs are at a high logic state. However, when the level shifted signal is inverted to a low logic state, the NAND gate 660 provides a high output to the output pulse triggering and noise rejection circuitry and to the NAND gate 650.

The output of the NAND gate 660 is also coupled to an inverter 670 and the D inputs of the flip-flops 606 and 608. The inverted output signal is applied to the input terminal of a Schmitt trigger and inverter block or Schmitt inverter 674 and to capacitor 672 which is charged by regulated voltage VDD. The output of the inverter 670 begins to discharge the capacitor 672 over a time constant that allows a specified delay before the Schmitt inverter 674 is triggered as shown by the delay between the signals in the lines 660 and 674 in FIG. 6. This allows some noise immunity to pulses which are shorter in duration than the delay.

The Schmitt inverter 674 responds after the time delay by generating a high output, pulse signal of the same duration as the ENBA and ENAB signals, but delayed. The high output signal passes through the exclusive OR or XOR gate 676 because the other input of XOR gate 676 is coupled to the Q output of flip-flop 606 and is already in a low logic state. However, as soon as the other input, coupled to the Q output of flip-flop 606, and the output of Schmitt inverter both go high, then the output of XOR gate 676 goes low, resulting in a short duration trigger pulse shown in line 676 of FIG. 6.

The delayed leading edge of the trigger pulse is applied to the TRIG input of the one shot 610 which responds to the positive going transition by providing a positive going, high logic state, output signal of a predetermined but relatively short duration, compared to the ENBA and ENAB signals, at its OSOUT terminal. The output signal is applied to the clock inputs C of the flip-flop 606 (through the XOR gate 678) and the flip-flop 608 and to the complementary clock inputs NC through inverters 680 and 682. The other input of XOR gate 678 is also at a logic low, as it is connected to the Q output of the flip-flop 606. As soon as the Q output goes high, then the output of XOR gate 678 again goes low, along with the output of the XOR gate 676, resulting in the short pulse depicted in line 676. The one shot 610 does not respond to signals at its TRIG input until it times out.

The output of the one shot 610 thus clocks a "1" into both flip-flops 606 and 608. The Q outputs go high, and the high state is applied to one input of the XOR gate 676 and the NAND gates 616 and 630. The output of XOR gate 678 goes high upon the time out of the one shot 610, but the re-clocking transition has no effect on the flip-flop 606 because its D input is still at the high state of the output of the NAND gate 660. Similarly, the transition to the low state of the one shot output signal has no effect on the state of flip-flop 608.

As described earlier, as long as the Q outputs of both flip-flops 606 and 608 are high and the ENABLE signal is present, FET 600 is rendered conductive and the FETs 601 and 602 are non-conducting. The voltage at VOUT is driven to VDD through the current limiting resistor 605.

When the ENBA or ENAB signal applied to VIN terminates, the output of NAND gate 660 goes low, and the D inputs to flip-flops 606 and 608 go low. At that point in time, the one shot 610 output from OSOUT would be low, and the output of XOR gate 678 and inverter 682 would be high. The low state at the input to the Schmitt inverter 674 also goes high, and, after a delay to charge capacitor 672, the Schmitt inverter 674 is triggered and its output goes low. Since the Q output of the flip flop 606 is high, the output of XOR gate 676 goes high. A high trigger signal pulse is thereby again provided to re-trigger one shot 610. The positive output pulse of one shot 610 is applied to an input of the XOR 678 which switches low at its output, since the other input remains high. The negative going transition of the clock signal does not affect the state of the flip-flop 606.

However, the positive going transition of the one shot output pulse triggers the flip-flop 608 to go low at its Q output. When the flip-flop 608 is clocked low, the output of NAND gate 616 goes high, turning FET 600 off and FET 601 on, and the transition of VOUT from the VDD to the VSS voltage level with a time constant related to the load capacitance and the resistances 603 and 605.

Flip-flop 606 is not clocked low until the termination of the one shot pulse which instigates a positive going transition at the output of XOR 678. When the pulse terminates, the output of XOR 678 transitions positively to the high state, clocking flip-flop 606 low. When this occurs, the state of NAND gate 630 switches high, causing FET 602 to conduct to the extent that it is forward biased. Thus the FET 600 is firmly turned off and the VOUT terminal is tied low by the tendency of FETs 601 and 602 to conduct.

Figure 7:
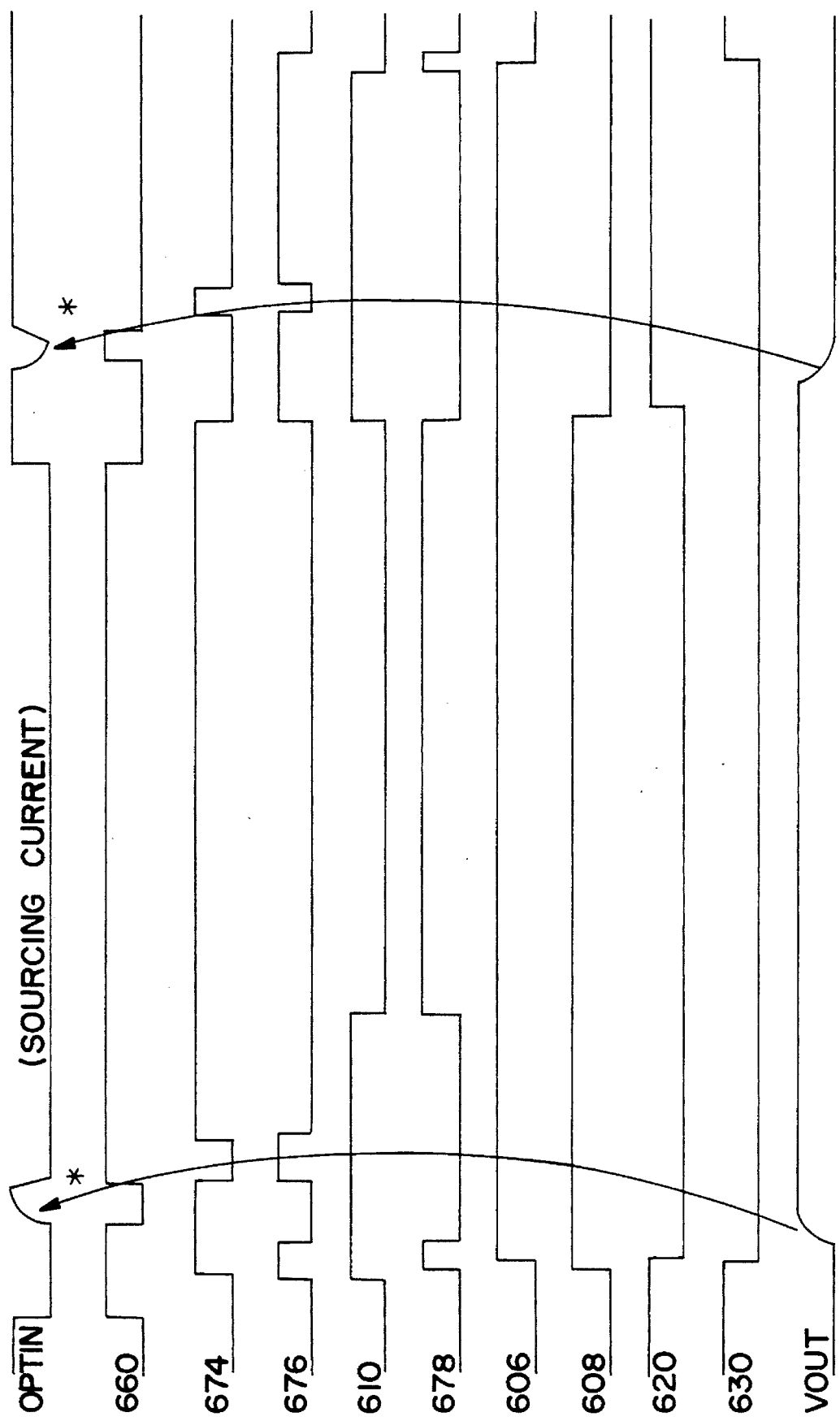
FIG. 7 is a timing diagram depicting a further operation of the circuit of FIG. 5 configured as a high side drive circuit in FIG. 4B.

Turning to the detailed use and function of the circuit of FIG. 5 as drive circuits U3 and U4, and in reference to FIGS. 4B and the timing diagram of FIG. 7, in this configuration the OPTIN terminals are coupled to the transistors of the opto-couplers 508 or 531. The VIN and CSEN input terminals are commonly connected to the other side of the transistors and are also coupled to VSS and the drains of IGTs 511 or 527. Thus, in the active quiescent state, the input signals at VIN and CSEN are low, and the OPTIN terminal state controls the delivery of the high side IGT gate drive current from terminals VOUT. Generally, the signals applied to the OPTIN input terminals are contemporaneous with the LED drive signals from the CSOUT terminals of the low side drive circuits U1, U2 which in turn are contemporaneous with the ENBA and ENAB command signals applied to the CSEN terminals. However, the OPTIN signal is affected by the high voltage transitions reflected back to the transistors of the opto-couplers 508 and 531 when the IGTs 511 and 527 conduct or cease conducting.

When the LED drive current is supplied from terminals CSOUT of drive circuits U1 and U2, the LEDs and photo-diodes of the opto-couplers conduct as described above, and current is drawn from the OPTIN terminal. The IVCONV block 612 is also specified to function as a current threshold detector. It is used as an input to determine if the current sinking through the external npn output stage (common emitter) of the opto-couplers from the OPTIN pin is of sufficient magnitude to be considered an asserted state, i.e. to detect the CSOUT signal provided by the associated low side drive circuit U1, U2. For a level of noise immunity, the IVCONV block 612 is specified to not detect any current less than 100 μA, but must detect current greater than 400 μA and must not source more than 400 μA to the OPTIN pin. The opto-coupler transistor will attempt to pull a minimum of 1 mA from OPTIN which will be easily detected considering the specified sensitivity.

The 400 μA current limit is specified to prevent depletion of the boot strapped power supply capacitors 509 and 540 at too rapid a rate. In this regard, the capacitor 509, for example, is charged from the regulated voltage through the resistor 506 and diode 507 and through the resistor 534 as soon as the regulated voltage level is achieved on charging of the capacitors C1, C2. When the IGT 511 is switched on, voltage at its source and across resistor 534 rapidly increases. The voltage on capacitor 509 is bootstrapped on the IGT 511 source voltage, and diode 507 is reverse biased. The VDD voltage that is then conducted to the VOUT terminal and applied to the gate maintains the forward bias and conduction of the IGT 511. The voltage on terminal VDD declines as current is drawn from capacitor 509 in order to power the components of FIG. 5, but not before the asserted pulse width is terminated.

Returning to the high side drive circuit operation of FIG. 5, when current is drawn within the specified range, the internal supply voltage at the OPTIN terminal falls below VREFL as shown in the OPTIN line in FIG. 7, and the output of the IVCONV block 612 switches to a low logic level. This switch to a low logic level causes the NAND gate 660 output to go high because the output of inverter 68 is normally high as shown in the second line of FIG. 7, since the VIN input is tied to VSS. Upon switching high at the output of NAND gate 660, the Schmitt inverter 674 and one shot 610 function as described above to provide the VDD voltage at terminal VOUT of each respective high side drive circuit U3, U4 as shown in FIG. 7.

When VDD is supplied at the VOUT terminal to the gate of the associated high side IGT and causes it to conduct as described above, up to 800 volts are presented at the common node of VIN, CSEN, VSS, and the emitter of the transistor of the opto-coupler, associated with the respective high side drive circuit U3, U4. The slew rate of the rise and fall time of the voltage at that node may transiently turn the photo-diode/transistor off, as shown in OPTIN line in relation to the VOUT line of FIG. 7. This interruption of the high output at NAND gate 660 allows capacitor 672 to momentarily recharge. The Schmitt inverter 674 may provide a narrow output pulse which causes the output of XOR 676 to go high as shown in the 676 line of FIG. 7 and re-trigger the one shot 610. However, when on, one shot 610 is not re-triggerable until it times out. Consequently, noise protection is achieved during the one shot time period which is set to cover the rise time of the high voltage biphasic pulse.

The same behavior is illustrated in FIG. 7 with respect to the transient effect on the OPTIN current level at the fall off of the VOUT signal. At that time, the one shot output is high since it was re-triggered by the positive going transition of the output of the XOR 676. The operation of the remainder of the circuit to produce the VDD signal level at the output VOUT remains the same as described above and as depicted in FIG. 7. The implementation of the preferred embodiment of the invention as described above is in the context of a biphasic wave form cardioverter/defibrillator. It will be understood that the wave form may be programmed in several ways with respect to delivered energy, including a single phase output by providing only one of the ENBA or ENAB commands. Moreover, it will be understood that the aspects of the invention implemented in the bridge output circuit for inhibiting the effects of noise may be implemented in single phase single or sequential pulse output circuits employing only a single high side drive circuit and high voltage switching IGT or a single branch employing a high and low side drive circuit and respective IGTs or equivalent high voltage switches.

Although an exemplary embodiment of the present invention has been shown and described, it will be apparent to those having ordinary skill in the art that a number of changes, modifications, or alterations to the invention as described herein may be made, none of which depart from the spirit of the present invention. All such changes, modifications and alterations should therefore be seen within the scope of the present invention.

What is claimed is:

1. A medical device for electrical termination of an arrhythmic condition of a patient's heart of the type comprising:

a battery;

means for detection of an arrhythmic condition of a patient's heart;

a high voltage capacitor;

controller means responsive to detection of an arrhythmic condition of said patient's heart, for initiating charging of said capacitor and for providing a discharge control signal;

converter means, responsive to said controller means, for providing charging current from said battery to said capacitor; and discharge circuit means for delivering voltage stored on said capacitor to said patient's heart in response to said discharge control signal, said discharge circuit means comprising:

high voltage switch means for connecting said capacitor to said patient's heart to discharge said capacitor through said patient's heart;

voltage regulating means coupled to said capacitor for sensing voltage stored on said capacitor and for generating a regulated voltage upon charging of said capacitor to a predetermined voltage;

drive circuit means powered by said regulated voltage and triggerable responsive to said discharge control signal for in turn triggering said high voltage switch means to discharge said capacitor; and means for inhibiting transient high voltage signals generated during switching of said high voltage switch means from re-triggering said drive circuit means.

2. The medical device of claim 1 wherein said inhibiting means further comprises:

time delay circuit means for delaying triggering of said drive circuit means in response to said discharge control signal until expiration of a delay interval; and one shot circuit means triggerable following said expiration of said delay interval for inhibiting response of said drive circuit means to interruption and restoration of said discharge control signal for a predetermined time period sufficient to prevent transient signals interrupting said discharge control signal from re-triggering said drive circuit means.

3. The medical device of claim 2 wherein said drive circuit means further comprises:

means responsive to generation of said regulated voltage for preventing triggering of said high voltage switch means absent said discharge control signal.

4. The medical device of claim 3 wherein:

said drive circuit means further comprises an output switch having an input terminal coupled to said voltage regulating means, an output terminal coupled to said high voltage switch means and a control terminal for conducting said regulated voltage to said output terminal in response to the discharge control signal; and said high voltage switch means has an input terminal coupled to said high voltage capacitor, an output terminal adapted to be coupled to the heart and a control terminal coupled to said output terminal of said output switch of said drive circuit means for conducting voltage on said high voltage capacitor to the output terminal upon conduction of the high voltage discharge switch means; said medical device further comprising:

bootstrap circuit means coupled between said output switch input terminal and said output terminal of said high voltage switch means for providing voltage at said output terminal of said high voltage switch means in addition to the regulated voltage to said output switch input terminal and, through conduction, to said control terminal of the high voltage switch means to maintain its conduction for the duration of the discharge control signal.

5. The medical device of claim 4 further comprising:

coupling means for providing a trigger signal at the input terminal of said drive circuit means and having an input means for receiving said discharge control signal and an isolated output means coupled to the input terminal of said drive circuit means and to said bootstrap circuit means for isolating said input means of said coupling means from high voltage at said bootstrap circuit means, whereby high voltage transitions on switching of said high voltage switch means at said isolated output means interrupt the trigger signal; and wherein:

said inhibiting means comprises one shot circuit means triggerable following expiration of said delay interval, for inhibiting transient signals interrupting said discharge control signal from re-triggering said drive circuit means.

6. The medical device of claim 1 wherein said drive circuit means further comprises:

means responsive to generation of said regulated voltage for triggering of said high voltage switch means absent said discharge control signal.

7. The medical device of claim 6 wherein:

said drive circuit means further comprises an output switch having an input terminal coupled to said voltage regulating means, an output terminal coupled to said high voltage switch means and a control terminal for conducting said regulated voltage to said output terminal of said drive circuit means in response to said discharge control signal;

said high voltage switch means has an input terminal coupled to said high voltage capacitor, an output terminal adapted to be coupled to the heart and a control terminal coupled to said output terminal of said output switch of said drive circuit means for conducting voltage on said high voltage capacitor to said output terminal upon triggering of said high voltage switch means; said medical device further comprising:

bootstrap circuit means coupled between said output switch input terminal and said output terminal of said high voltage switch means for providing voltage at the output terminal of said high voltage switch means in addition to the regulated voltage to the output switch input terminal and, through conduction, to the control terminal of said high voltage switch means to maintain its conduction for the duration of the discharge control signal.

8. The medical device of claim 7 further comprising:

coupling means for providing a trigger signal at the input terminal of said drive circuit and having an input means for receiving said discharge control signal and an isolated output means coupled to the input terminal of said drive circuit means and to said bootstrap circuit means for isolating said input means of said coupling means from high voltage at said bootstrap circuit means, whereby high voltage transitions on switching of said high voltage switch means at said isolated output portion interrupt the trigger signal; and wherein:

said inhibiting means comprises one shot circuit means triggerable following said delay interval, for inhibiting transient signals interrupting discharge control signal from re-triggering said drive circuit means.

9. The medical device of claim 1 wherein:

said drive circuit means further comprises an output switch having an input terminal coupled to said voltage regulating means, an output terminal coupled to said high voltage discharge control switch and a control terminal for conducting said regulated voltage to said output terminal in response to said discharge control signal;

said high voltage switch means has an input terminal coupled to said high voltage capacitor, an output terminal adapted to be coupled to the heart and a control terminal coupled to said output terminal of said output switch for conducting voltage on said high voltage capacitor to the output terminal of said high voltage switch means;

and further comprising:

bootstrap circuit means coupled between said output switch input terminal and said output terminal of said high voltage switch means for providing voltage at the output terminal of said high voltage switch means in addition to the regulated voltage to the output switch input terminal and, through conduction, to the control terminal of the high voltage switch means to maintain its conduction for the duration of the discharge control signal.

10. The medical device of claim 9 further comprising:

coupling means for providing a trigger signal at the input terminal of said drive circuit and having an input means for receiving said discharge control signal and an isolated output means coupled to the input terminal of said drive circuit means and to said bootstrap circuit means for isolating said input means of said coupling means from high voltage at said bootstrap circuit means, whereby high voltage transitions on switching of said high voltage switch means interrupt the trigger signal; and wherein:

said inhibiting means comprises one shot circuit means triggerable following said delay interval, for inhibiting transient signals interrupting said discharge control signal from re-triggering said drive circuit means.

11. A medical device for electrical termination of an arrhythmic condition of a patient's heart by delivery of biphasic stimulation pulses sequentially in opposing directions through said patient's heart comprising:

a battery;

means for detection of an arrhythmic condition of said patient's heart;

a high voltage capacitor;

controller means responsive to detection of an arrhythmic condition of said patient's heart for initiating a charging of said high voltage capacitor and for providing first and second discharge control signals in sequence;

converter means, responsive to said controller means, for providing charging current from said battery to said high voltage capacitor; and high voltage discharge means for delivering voltage stored on said high voltage capacitor to said patient's heart in response to said first and second discharge control signals, said high voltage discharge means further comprising:

first high and low side drive circuit means for providing first high and low side trigger signals in response to said first discharge control signal;

second high and low side drive circuit means for providing second high and low side trigger signals in response to said second discharge control signal;

first discharge circuit means having first high and low side voltage discharge switches switchable into conduction by said first high and low side trigger signals for connecting said high voltage capacitor with said patient's heart, for discharging high voltage through said patient's heart in a first direction;

second discharge circuit means having second high and low side voltage discharge switches switched into conduction by said second high and low side trigger signals for connecting said high voltage capacitor means with said patient's heart, for discharging high voltage through said patient's heart in a second direction; and wherein said first and second high side drive circuit means further comprise means for inhibiting transient high voltage signals generated during switching of said first and second high side voltage discharge switches and coupled back to said first and second high side drive circuit means from re-triggering said first and second high side voltage discharge switches.

* * * * *

UNITED STATES PATENT AND TRADEMARK OFFICE
CERTIFICATE OF CORRECTION

PATENT NO. : 5,470,341
DATED : November 28, 1995
INVENTOR(S) : Kuehn et al.

It is certified that error appears in the above-indentified patent and that said Letters Patent is hereby corrected as shown below:

Col. 9, line 35 should be deleted and the following should be inserted therefor:

--Period = $Ton + \frac{K}{IF} + Vm/R$, where:

$Ton$ = the fixed "on" time;
$IF$ = a constant current used to set the maximum "off" time when $Vm = O$;
$K$ = a constant used with IF to set the maximum "off" time when $Vm = O$; and
$R$ = value of the resistor placed between Vm and ground to set a current which adds to IF to decrease the "off" time.--

Col. 10, line 67: delete "US" and insert in its stead --U8--.

Signed and Sealed this

First Day of October, 1996

Attest:

BRUCE LEHMAN

*Attesting Officer*  *Commissioner of Patents and Trademarks*